(12) United States Patent
Kroll

(10) Patent No.: US 6,576,143 B2
(45) Date of Patent: Jun. 10, 2003

(54) METHOD FOR THE REMOVAL OF SULFIDE INTERFERENCE IN COMMON TESTS FOR ARSENIC

(75) Inventor: Dan J. Kroll, Ft. Collins, CO (US)

(73) Assignee: Hach Company, Loveland, CO (US)

( * ) Notice: Subject to any disclaimer, the term of this patent is extended or adjusted under 35 U.S.C. 154(b) by 57 days.

(21) Appl. No.: 09/777,196

(22) Filed: Feb. 2, 2001

(65) Prior Publication Data

US 2002/0000414 A1 Jan. 3, 2002

Related U.S. Application Data

(60) Provisional application No. 60/193,863, filed on Mar. 30, 2000.

(51) Int. Cl.⁷ .................................................. C02F 1/72
(52) U.S. Cl. ........................................ 210/758; 210/759
(58) Field of Search .................................. 210/758, 759

(56) References Cited

U.S. PATENT DOCUMENTS 5,207,927 A * 5/1993 Marinangeli et al.
5,470,486 A * 11/1995 Gillespie

* cited by examiner

Primary Examiner—Betsey Morrison Hoey
(74) Attorney, Agent, or Firm—Dean P. Edmundson

(57) ABSTRACT

A method for removing sulfide from a liquid sample such as water in a test for arsenic. The method involves adding a strong oxidizing agent to the sample to oxidize the sulfide to sulfate, and then adding an organic amine to the sample to react with any remaining oxidizing agent.

6 Claims, No Drawings

METHOD FOR THE REMOVAL OF SULFIDE INTERFERENCE IN COMMON TESTS FOR ARSENIC

CROSS-REFERENCE TO RELATED APPLICATION

This application is based upon, and claims the benefit of, my Provisional Application No. 60/193,863, filed Mar. 30, 2000.

FIELD OF THE INVENTION

This invention relates to arsenic testing in all matrixes in which sulfide interference is likely to be encountered including groundwater, surface water, drinking water, industrial and municipal wastewater. More particularly, this invention relates to removing interferences caused by the presence of sulfides in the water when testing for arsenic.

BACKGROUND OF THE INVENTION

Arsenic is a common contaminant of groundwater that has been found to cause adverse effects on human health at levels as low as 10 µg/L. The most common forms of dissolved arsenic are arsenite and arsenate. The chemistry of dissolved arsenic is very similar to that of phosphate, which makes its analytic quantification problematic, because phosphate interferes. The most effective method for eliminating the interference caused by phosphate is by separating the arsenic from the phosphate by reducing the arsenic to arsine gas ($AsH_3$). The most common technique for the field detection of arsenic is a modified Gutzeit test. In this test, arsenic is reduced in the presence of zinc and hydrochloric acid to form arsine gas ($AsH_3$), as follows:

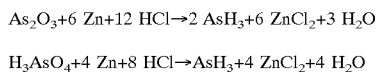

$H_3AsO_4 + 4\ Zn + 8\ HCl \rightarrow AsH_3 + 4\ ZnCl_2 + 4\ H_2O$

Other combinations of mineral acids and metals may be used in the reduction such as sulfamic acid and zinc, as follows:

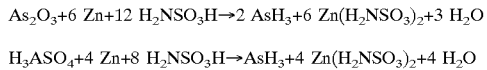

$H_3ASO_4 + 4\ Zn + 8\ H_2NSO_3H \rightarrow AsH_3 + 4\ Zn(H_2NSO_3)_2 + 4\ H_2O$ In the Gutzeit test the liberated arsine gas is then reacted with a detector paper that has been impregnated with mercuric bromide (HgBr). The arsine reacts with the mercuric bromide to form mixed arsenic mercury halogenides and create a yellow to tan to brown color change.

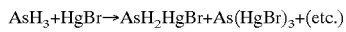

In the most common photometric method for the detection of arsenic (silver diethyldithiocarbamate method), the generation of arsine is also used to remove interferences. In this method the silver diethyldithiocarbamate is dissolved in pyridine. The generated arsine gas is then bubbled through this solution. Arsine reacts with the silver salt, forming a soluble red complex suitable for photometric measurement.

Unfortunately, during the generation of arsine gas by reduction in these tests, sulfides are also reduced concurrently with the arsenic to form hydrogen sulfide ($H_2S$). Hydrogen sulfide also reacts with the indicators for arsenic (mercuric bromide, silver diethyldithiocarbamate, etc.) to form colored complexes that interfere with the detection of arsenic.

Sulfides are commonly found in water samples and can be present in varying amounts. Sulfide is a poisonous by-product of anaerobic decomposition of organic matter and is almost ubiquitous in sewage and industrial wastewater. Sulfide is also commonly present in groundwater, especially hot springs. Waters that contain sulfides are commonly known as "sulfur waters". Their most noticeable characteristic is their offensive, rotten-egg odor. The threshold odor concentration of $H_2S$ in clean water is between 0.025 and 0.250 µg/L. When present to the extent of 1 mg/L, it becomes very offensive.

Groundwater will commonly range from 0–70 mg/L sulfide. Groundwater having higher amounts of sulfide is occasionally encountered, but waters with above 5 mg/L are seldom considered usable.

Sulfide interferes with common methods of arsenic detection on a 1:1 molar ratio. (Molecular weight of As=74.92: Molecular Weight of $H_2S$=32.074). Therefore, the levels of sulfide commonly encountered in nature are a serious problem when trying to detect arsenic in the parts per billion range.

The current methods of removing sulfide interference entail passing the arsine gas stream through a scrubber to remove hydrogen sulfide. These scrubbers are usually cotton soaked in lead acetate solution (zinc and copper have also been utilized but have been found to be less efficient). The sulfide reacts with the lead on the cotton to form solid lead sulfide, thus removing the sulfide contaminant from the arsine gas stream.

There are two major drawbacks to this method. First, it is difficult to ensure that a tight seal has been formed that will obligate the passage of all of the gas through the scrubber. The rate of gas evolution must also be controlled to allow adequate contact time for all of the sulfide to react. Secondly, the operator is forced to handle hazardous lead acetate and lead sulfide, and after the test is over, there remains the problem of disposing of these toxic materials.

There has not heretofore been provided a reliable method for the removal of sulfide interference from arsenic tests that is effective and does not utilize hazardous materials.

SUMMARY OF THE INVENTION

In accordance with the present invention, there is provided an improved test for arsenic in a water sample when sulfides are present. The improvement involves the use of a strong oxidizing agent to oxidize sulfide to sulfate in which form it no longer interferes. The strong oxidant must thereafter be eliminated from the sample to prevent it from interfering in the subsequent reduction step and the evolution of arsine gas. This requires a strong oxidant that is capable of oxidizing sulfide to sulfate and then itself can be easily removed from the sample. Potassium peroxymonopersulfate (which is commercially available from DuPont as Oxone®) satisfies this requirement.

The active ingredient of the Oxone® product is potassium peroxymonopersulfate, $KHSO_5$, commonly known as potassium monopersulfate, which is present as a triple salt with the formula $2KHSO_5 \cdot KHSO_4 \cdot K_2SO_4$ (potassium hydrogen peroxymonosulfate sulfate). The oxidation potential of Oxone® is derived from its peracid chemistry; it is the first neutralization salt of peroxymonosulfuric acid $H_2SO_5$ (also known as Caro's acid).

The standard electrode potential ($E^0$) of Oxone® is shown in the following reaction:

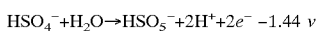

This potential is high enough for many room temperature oxidations to occur, including the oxidation of sulfide to sulfate. Oxone® has been used to oxidize hydrogen sulfide in waste streams for odor control.

There are other readily available oxidants that have the capability of oxidizing sulfide to sulfate, such as Hydrogen Peroxide ($E^0 = -1.766$ v). The problem is that they interfere with the second portion of the arsenic test, which is the reduction of arsenic to arsine gas, and they are also dangerous and difficult to handle. Potassium peroxymonopersulfate offers the advantages of being, safe, easy to handle, and also being easy to eliminate from the sample before the reduction step.

Oxone® (i.e. potassium peroxymonopersulfate) is quickly removed from the sample, after all of the sulfide has been oxidized, by the addition of organic amines, which are readily attacked by the Oxone® thus depleting its oxidizing power. Useful compounds for this elimination include ethylenediaminetetraacetic acid {also known as EDTA}, N,N-bis-(hydroxyethyl)-2-aminoethane sulfonic acid {also known as BES}, and N,N-bis-(2-hydroxyethyl) glycine {also known as Bicine}.

Use of Oxone® with an appropriate buffer followed by removal of the Oxone® with one of the above substances allows for the detection of arsenic without interference from sulfide. A 50 mL sample of water containing 5 mg/L sulfide as $H_2S$ can be effectively cleared of sulfide interference by adding 0.45–0.55 g of a buffer consisting of dipotassium phosphate to adjust the final pH to an appropriate level for sulfide oxidation when the Oxone® is present (pH 6–8). Then 0.6–0.7 g of Oxone® is added to oxidize the sulfide. The Oxone® can then be quickly eliminated by addition of one of the above mentioned amines, for example 0.6–0.7 g of a 1:1 mixture of tetrasodium and disodium EDTA.

Samples that contained 5 mg/L $H_2S$ and no arsenic, treated with the above procedure and quantified using arsine generation (2.5 g of sulfamic acid and 1.6 g of 100 mesh zinc per 50 mL sample) and mercuric bromide paper, showed no visual difference from a DI water blank that was not treated for sulfide removal and was only put through the arsine generation steps and detection steps. Both read 0 µg/L arsenic. A sample that contained 5 mg/L $H_2S$ and no arsenic that was not treated with Oxone®, but was just put through the arsine generation and detection procedure read over the maximum level of the test which is 500 µg/L arsenic. A third set of samples that contained 10 µg/L arsenic and 5 mg/L $H_2S$ were put through the Oxone® treatment and arsine generation. These samples read 10 µg/L.

Results of Sulfide Treatment Using Mercuric Bromide Detection

| Sample | Oxone Treatment (Y/N) | Results |
|---|---|---|
| DI Water | N | 0 µg/L |
| DI Water | Y | 0 µg/L |
| 5 mg/L $H_2S$ | Y | 0 µg/L |
| 5 mg/L $H_2S$ | N | >500 µg/L |
| 5 mg/L $H_2S$ + 10 µg/L As | Y | 10 µg/L |
| 5 mg/L $H_2S$ + 10 µg/L As | N | >500 µg/L |

Similar tests were performed using silver diethyldithiocarbamate dissolved in pyridine as the indicator (1 g per 200 mL pyridine). A 250 mL sample was used, therefore the weight of all reagents was multiplied by a factor of 5 compared to the weights used for the 50 mL sample above. Results were read in a 1 inch cell at 520 nm.

Results of Sulfide Treatment Using Silver Diethyditiocarbamate Detection

| Sample | Oxone Treatment (Y/N) | Results |
|---|---|---|
| DI Water | Y | 0 µg/L |
| DI Water | N | 0 µg/L |
| 5 mg/L $H_2S$ | Y | 0 µg/L |
| 5 mg/L $H_2S$ | N | >1000 µg/L |
| 100 µg/L As | Y | 96.4 µg/L |
| 100 µg/L As | N | 100 µg/L |
| 5 mg/L $H_2S$ + 10 µg/L As | Y | 97.4 µg/L |
| 5 mg/L $H_2S$ + 10 µg/L As | N | >1000 µg/L |

Thus, as illustrated above, this new method of sulfide removal from an arsenic test is quick and easy to use. It is very effective and it is free of hazardous reagents or waste. It offers distinct advantages over the current used method of lead acetate scrubbing. The new method has been demonstrated to work in conjunction with the two most common indicators for arsenic and is expected to work with any other detection method that is combined with arsine generation.

What is claimed is:

1. A method for removing sulfide from a liquid sample in a test for arsenic, the method comprising:

(a) adding a strong oxidizing agent to said sample to oxidize the sulfide to sulfate;

(b) adding an organic amine to said sample to react with any remaining oxidizing agent.

2. The method in accordance with claim 1, wherein said oxidizing agent comprises potassium peroxymonopersulfate.

3. The method in accordance with claim 1, wherein said organic amine is selected from the group consisting of: EDTA, BES, and Bicine.

4. The method in accordance with claim 1, comprising the further step of adjusting the pH of said sample to the range of 6 to 8 prior to adding said oxidizing agent.

5. The method in accordance with claim 4, wherein said pH is adjusted by means of addition of dipotassium phosphate to said sample.

6. The method in accordance with claim 1, wherein said liquid sample comprises water.

* * * * *